(12) United States Patent
Miao et al.

(10) Patent No.: US 9,101,634 B2
(45) Date of Patent: Aug. 11, 2015

(54) APPLICATION OF 2, 3-DIHYDRO-3-HYDROXYMETHYL-6-AMINO-[1,4]-BENZOXAZINE IN PREPARATION OF DRUGS INDUCING EMBRYONIC STEM CELLS TO DIFFERENTIATE TO VASCULAR ENDOTHELIAL CELLS

(75) Inventors: Junying Miao, JiNan (CN); Baoxiang Zhao, JiNan (CN); Shangli Zhang, JiNan (CN); Jing Zhao, JiNan (CN); Le Su, JiNan (CN); Lei Han, JiNan (CN)

(73) Assignee: SHANDONG UNIVERSITY, Jinan (CN)

( * ) Notice: Subject to any disclaimer, the term of this patent is extended or adjusted under 35 U.S.C. 154(b) by 908 days.

(21) Appl. No.: 13/378,451

(22) PCT Filed: May 10, 2011

(86) PCT No.: PCT/CN2011/000810
§ 371 (c)(1),
(2), (4) Date: Dec. 15, 2011

(87) PCT Pub. No.: WO2011/143927
PCT Pub. Date: Nov. 24, 2011

(65) Prior Publication Data
US 2012/0123116 A1   May 17, 2012

(30) Foreign Application Priority Data
May 20, 2010   (CN) .......................... 2010 1 0177138

(51) Int. Cl.
*A61K 31/538* (2006.01)
(52) U.S. Cl.
CPC .................................. *A61K 31/538* (2013.01)
(58) Field of Classification Search
CPC .................................................. A61K 31/538
See application file for complete search history.

(56) References Cited

U.S. PATENT DOCUMENTS

| | | |
|---|---|---|
| 3,879,522 A | 4/1975 | Pesson |
| 6,649,610 B1 | 11/2003 | Miles et al. |
| 6,872,823 B1 | 3/2005 | Sato et al. |
| 2006/0149461 A1 | 7/2006 | Rowley et al. |

FOREIGN PATENT DOCUMENTS

| | | |
|---|---|---|
| CN | 101084902 A | 12/2007 |
| CN | 101185651 A | 5/2008 |
| CN | 101836993 A | 9/2010 |
| GB | 883324 | 11/1961 |
| GB | 1173942 | 12/1969 |
| GB | 1182770 | 3/1970 |
| GB | 1 285 711 | 8/1972 |
| JP | A-2000-327663 | 11/2000 |
| WO | WO 89/07596 A1 | 8/1989 |
| WO | WO 02/30914 A1 | 4/2002 |
| WO | WO 2004/087694 A1 | 10/2004 |
| WO | WO 2005/051934 A1 | 6/2005 |
| WO | WO 2005/058847 A1 | 6/2005 |

OTHER PUBLICATIONS

Filipczyk et al, Stem Cell Research, 2007, 1:45-60.*
Dong et al, J Cell Physiol, 2010, 223:202-208.*
International Search Report issued in International Application No. PCT/CN2011/000810 on Aug. 11, 2011 (with translation).
Written Opinion of the International Searching Authority issued in International Application No. PCT/CN2011/000810 on Aug. 11, 2011 (with partial translation).

* cited by examiner

*Primary Examiner* — Marcia S Noble
*Assistant Examiner* — Chi-Feng Hsu
(74) *Attorney, Agent, or Firm* — Oliff PLC (57) ABSTRACT

An application of 2,3-dihydro-3 hydroxymethyl-6-amino-[1,4]-benzoxazine in the preparation of drugs inducing embryonic stem cells to differentiate to vascular endothelial cells, wherein the concentration of the 2,3-dihydro-3 hydroxymethyl-6-amino-[1,4]-benzoxazine in the preparation of drugs effectively inducing mouse embryonic stem cells to differentiate to vascular endothelial cells is 1~20 µM. The 2,3-dihydro-3 hydroxymethyl-6-amino-[1,4]-benzoxazine provided by the invention lays foundation for preparing and developing drugs inducing embryonic stem cells to differentiate to vascular endothelial cells, can be used as an effective research tool of embryonic stem cells, and can be used for researching on embryonic stem cell differentiation and new molecular mechanisms of blood vessel formation.

4 Claims, 4 Drawing Sheets

APPLICATION OF 2, 3-DIHYDRO-3-HYDROXYMETHYL-6-AMINO-[1,4]-BENZOXAZINE IN PREPARATION OF DRUGS INDUCING EMBRYONIC STEM CELLS TO DIFFERENTIATE TO VASCULAR ENDOTHELIAL CELLS

BACKGROUND

1. Field of Invention

This invention relates to the purpose of benzoxazine derivative, in particular to application of 2,3-dihydro-3-hydroxymethyl-6-amino-[1,4]-benzoxazine in preparation of drugs inducing embryonic stem cells to differentiate to vascular endothelial cells.

2. Description of Related Art

The structural formula of 2,3-dihydro-3-hydroxymethyl-6-amino-[1,4]-benzoxazine is as follows:

Molecular formula: $C_9H_{12}N_2O_2$

Molecular weight: 180.2 Property: light yellow solid, melting point: 154-156° C. 2,3-dihydro-[1,4]-benzoxazine derivative belongs to a kind of very important structural units, and many natural products and synthetic drugs contain the structural unit.

The known 2,3-dihydro-2-substituted-[1,4]-benzoxazine derivatives have pharmacological activities of resisting bacteria, thrombus, bradycardia, central nervous system (CNS) disorders and the like, such as 2,3-dihydro-2-substituted-[1,4]-benzoxazine derivative structures involved in patents with the patent No. of U.S. Pat. No. 6,649,610, WO2005051934 and WO2005058847; 2,3-dihydro-2,3-substituted-[1,4]-benzoxazine derivatives are provided with pharmacological activities of analgesic, sedative, laxative and the like, such as 2,3-dihydro-2,3-substituted-[1,4]-benzoxazine derivative structures involved in patents with the patent numbers of GB1285711, GB1182770 and GB883324. In addition, 2,3-dihydro-[1,4]-benzoxazine compounds containing substituent on other locations (such as nitrogen and benzene ring) have the pharmacological effects of muscle relaxant, analgesic, anti-psychiatric disorders, anti-Parkinson, anti-inflammation, antipyretic, prevention of coronary heart disease and atherosclerosis, inhibition of phosphodiesterase and the like, such as 2,3-dihydro-[1,4]-benzoxazine derivative structures involved in patents with the patent numbers of U.S. Pat. No. 3,879,522, GB1173942, WO8907596, WO2004087694, WO0230914 and JP2000327663. However, people's research on structures, activity and synthesis of 2,3-dihydro-3-substituted-[1,4]-benzoxazine derivatives is rare, only including 2,3-dihydro-3-methyl-[1,4]-benzoxazine derivatives involved in patents with the patent numbers of U.S. Pat. No. 6,872,823 and US2006014946, and the compounds are mainly used as important intermediate for synthesizing quinolone antibacterial drugs and plant protection agents. The preparation methods include: 1) Three-step reaction preparation with 2,3,4-trifluoro-aniline and 2-hydroxy-propionate as raw materials, involved in U.S. Pat. No. 6,872,823; 2) Reduction preparation with 5% Pt/C by the aid of o-phenoxy acetone in isopropyl alcohol, involved in U.S. Patent US2006014946.

According to retrieval by the authority, the research on 2,3-dihydro-3-hydroxymethyl-6-amino-[1,4]-benzoxazine inducing embryonic stem cells to differentiate to vascular endothelial cells has not been reported at home and abroad currently.

SUMMARY

The problem to be solved by the invention is to provide an application of 2,3-dihydro-3-hydroxymethyl-6-amino-[1,4]-benzoxazine in the preparation of drugs inducing embryonic stem cells to differentiate to vascular endothelial cells aiming at the deficiency in existing technology.

The invention describes the application of 2,3-dihydro-3-hydroxymethyl-6-amino-[1,4]-benzoxazine in preparation of drugs inducing embryonic stem cells to differentiate to vascular endothelial cells.

Wherein, the concentration of the 2,3-dihydro-3-hydroxymethyl-6-amino-[1,4]-benzoxazine in the preparation of drugs effectively inducing mouse embryonic stem cells to differentiate to vascular endothelial cells is 1~20 μM, and the optimal concentration is 10 μM.

The 2,3-dihydro-3-hydroxymethyl-6-amino-[1,4]-benzoxazine provided by the invention lays foundation for researching and developing drugs promoting the generation of vascular endothelial cells. The 2,3-dihydro-3-hydroxymethyl-6-amino-[1,4]-benzoxazine provided by the invention also can be used as an effective tool and used for research on molecular mechanism that embryonic stem cells differentiate to endothelial cells.

Next, pharmacological experiments and results of 2,3-dihydro-3-hydroxymethyl-6-amino-[1,4]-benzoxazine are used for illustrating its application of inducing embryonic stem cell to differentiate to the vascular endothelial cells in order to better understand the essence of the invention.

Preparation of 2,3-dihydro-3-hydroxymethyl-6-amino-[1,4]-benzoxazine in the invention Iron powder (0.670 g, 12 mmol) was added into EtOH/H2O (v/v=6:1, 100 mL) solution of 2,4-dinitrophenyl glycidyl ether (0.480 g, 2 mmol) and acetic acid (1 mL, 17.5 mmol) at reflux temperature. The reaction mixture was refluxed continuously for 120 minutes, and cooled to room temperature, saturated Na2CO3 solution was used for adjusting pH=8, the solution was leached out with C salt for concentrating ethanol and water in the filtrate, and the solid ethanol was obtained (10 mL×4). Ethanol phase was dried with anhydrous MgSO4 and filtered to obtain crude products; the above crude products were separated with silica gel column chromatography (ethanol as developing agent), and 2,3-dihydro-3-hydroxymethyl-6-amino-[1,4]-benzoxazine (0.149 g, 42%) was prepared.

Cell biology and molecular biology methods were adopted to study and validate the function of the 2,3-dihydro-3-hydroxymethyl-6-amino-[1,4]-benzoxazine of the invention to induce embryonic stem cells to differentiate to vascular endothelial cells with the following experiments.

1. The Influence of 2,3-dihydro-3-hydroxymethyl-6-amino-[1,4]-benzoxazine on Mouse Embryonic Stem Cell Morphology;

The embryonic stem cells were evenly grown in a 24-well plate, a normal group was set after the cells adhered on the wall: the normal group was cultured under the condition of differentiation culture medium (after removal of leukemia inhibitory factor from normal culture medium); solvent control group: the group was cultured after DMSO was added under the culture condition of differentiation culture medium; experimental group: the group was cultured after 2,3-dihydro-3-hydroxymethyl-6-amino-[1,4]-benzoxazine with the concentration of 0.5 μM~40 μM was added under the culture condition of differentiation culture medium. The culture conditions: 37° C., CO2 incubator box for cultivation. The culture medium should be replaced everyday in a timing mode, the morphological changes were observed under an inverted phase contrast microscope until the tenth day.

Figure 1:
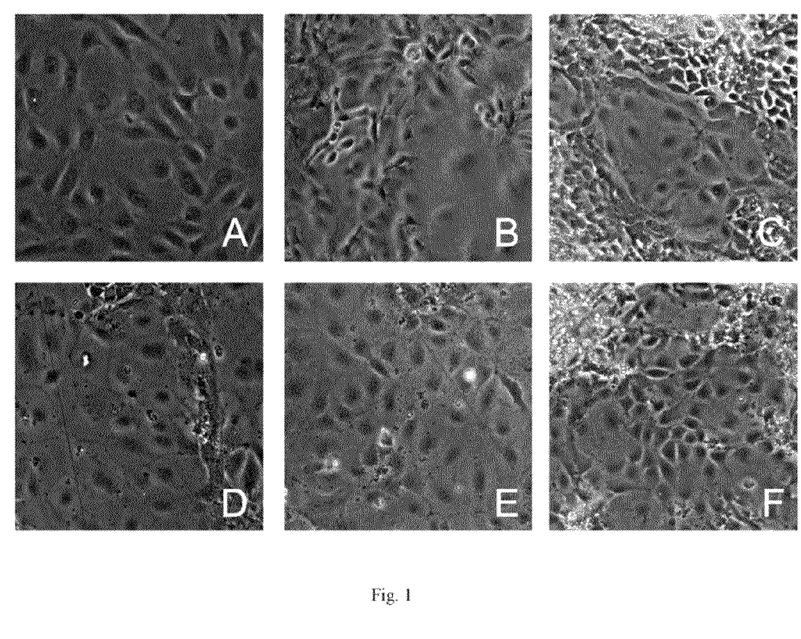
FIG. 1 is the form picture of embryonic stem cells after 2,3-dihydro-3-hydroxymethyl-6-amino-[1,4]-benzoxazine induces embryonic stem cells for ten days, which is displayed under an inverted phase contrast microscope, under the culture condition that leukemia inhibitory factor is not contained.
Wherein:
A: A refers to human umbilical vein endothelial cells as positive control;
B: The embryonic stem cells are naturally differentiated for ten days under the culture condition that eukemia inhibitory factor is not contained.
C: The embryonic stem cells are differentiated for ten days after DMSO is added under the culture condition that eukemia inhibitory factor is not contained.
D: The embryonic stem cells are induced for ten days after 2,3-dihydro-3-hydroxymethyl-6-amino-[1,4]-benzoxazine with the concentration of 5 μM is added under the culture condition that eukemia inhibitory factor is not contained.
E: The embryonic stem cells are induced for ten days after 2,3-dihydro-3-hydroxymethyl-6-amino-[1,4]-benzoxazine with the concentration of 10 μM is added under the culture condition that eukemia inhibitory factor is not contained.
F: The embryonic stem cells are induced for ten days after 2,3-dihydro-3-hydroxymethyl-6-amino-[1,4]-benzoxazine with the concentration of 20 μM is added under the culture condition that eukemia inhibitory factor is not contained.

The results showed that: compared with the normal group and the solvent control group, the 1~20 μM treatment group in the experimental group was changed compared with the cell morphology of the control group ten days after differentiation, the cell forms of the 10 μM treatment group had significant changes (see FIG. 1), the previous typical embryonic stem cells with aggregation growth were cloned to form vascular endothelial cell-forms, the cell body gradually was retracted with strong three-dimensional enhancement; while the cell form changes of other treatment groups in the experimental group were relatively weak.

2. Detection of Vascular Endothelial Cell Markers (Flk-1)

The embryonic stem cells which were induced with 2,3-dihydro-3-hydroxymethyl-6-amino-[1,4]-benzoxazine with the concentration of 0.5 μM~40 μM for 5 days and 10 days were evenly grown in 48-well plate and cultured for 24 hours in CO2 incubation chamber at 37° C., after the cells adhered on the wall, immunohistochemistry and laser scanning confocal microscopy were used for observing the expression of endothelial cell markers—Flk-1 The normal group was set: the group was cultured in under the culture condition of differentiation culture medium; solvent control group: the group was cultured after DMSO was added under the culture condition of differentiation culture medium; experimental group: the group was cultured after 2,3-dihydro-3-hydroxymethyl-6-amino-[1,4]-benzoxazine with the concentration of 0.5 μM~40 μM was added under the culture condition of differentiation culture medium.

Figure 2:
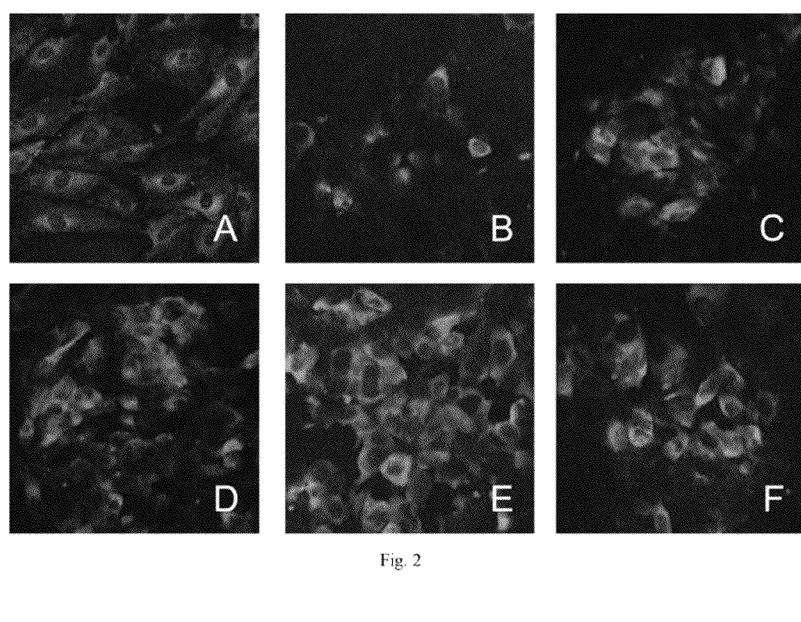
FIG. 2 is the expression condition of vascular endothelial marker Flk-1 after embryonic stem cells are induced for ten days with 2,3-dihydro-3-hydroxymethyl-6-amino-[1,4]-benzoxazine, which is displayed under a laser confocal microscope, under the culture condition that embryonic stem cells do not contain eukemia inhibitory factor.
Wherein:
A: A refers to human umbilical vein endothelial cells as positive control.
B: Embryonic stem cells are naturally differentiated for ten days under the culture condition that leukemia inhibitory factor is not contained.
C: Embryonic stem cells are induced for ten days after DMSO is added under the culture condition that leukemia inhibitory factor is not contained.
D: Embryonic stem cells are induced for ten days after 2,3-dihydro-3-hydroxymethyl-6-amino-[1,4]-benzoxazine with the concentration of 5 μM is added under the culture condition that leukemia inhibitory factor is not contained.
E: Embryonic stem cells are induced for ten days after 2,3-dihydro-3-hydroxymethyl-6-amino-[1,4]-benzoxazine with the concentration of 10M is added under the culture condition that leukemia inhibitory factor is not contained.
F: Embryonic stem cells are induced for ten days after 2,3-dihydro-3-hydroxymethyl-6-amino-[1,4]-benzoxazine with the concentration of 20 μM is added under the culture condition that leukemia inhibitory factor is not contained.

The results showed that: After induction for 10 days, the expression of vascular endothelial cell marker Flk-1 in the experimental group was gradually increased, only a few amount of expression of Flk-1 was increased in the normal group and the solvent control group, the expression of 2 3-dihydro-3-hydroxymethyl-6-amino-[1,4]-benzoxazine Flk-1 with the concentration of 1 μM~20 μM in the experiment group was increased, the expression increase of embryonic stem cells in the 10 μM treatment group was more obvious (see FIG. 2). It is indicated that 10 μM 2,3-dihydro-3-hydroxymethyl-6-amino-[1,4]-benzoxazine can significantly induce embryonic stem cells to differentiate to vascular endothelial cells.

3. Detection of Vascular Endothelial Cell Marker (CD31)

The embryonic stem cells induced by 2,3-dihydro-3-hydroxymethyl-6-amino-[1,4]-benzoxazine with the concentration of 0.5 μM~40 μM for ten days were cracked, and total cellular protein was distilled. The solvent control group was set: the group was cultured after DMSO was added under the culture condition of differentiation culture medium; experimental group: the group was cultured after 2,3-dihydro-3-(hydroxymethyl)-6-Amino-[1,4]-benzoxazine with the concentration of 0.5 μM~40 μM under the culture condition of differentiation culture medium. The extracted embryonic stem cells were used for Western blot experiment to detect the expression of vascular endothelial marker CD31.

Figure 3:
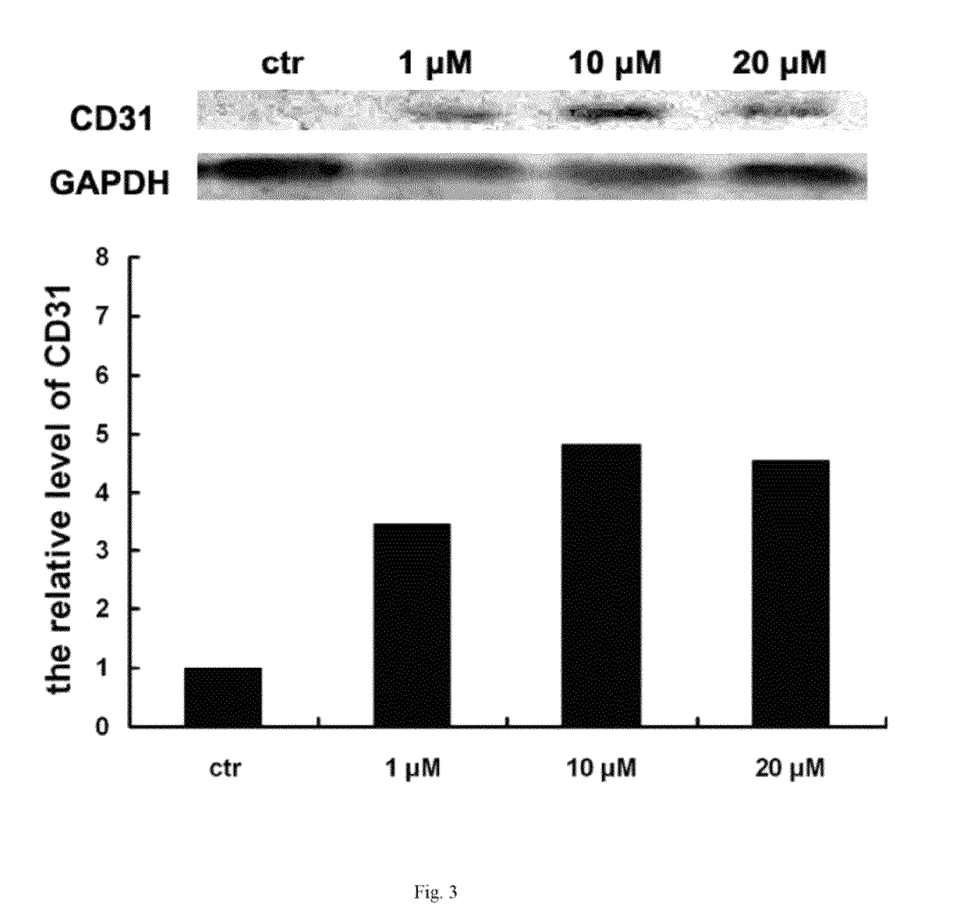
FIG. 3 is the expression amount of vascular endothelial marker CD31 after embryonic stem cells are induced for ten days with 2,3-dihydro-3-hydroxymethyl-6-amino-[1,4]-benzoxazine, which is detected with western blot, under the culture condition that embryonic stem cells do not contain eukemia inhibitory factor.

The results showed that: After induction of 10 days, the expression of vascular endothelial cell marker CD31 in the experimental group was increased compared with the solvent control group, the 2,3-dihydro-3-(hydroxymethyl)-6-amino-[1,4]-benzoxazine with the concentration of 1 μM~20 μM in the experimental group had increased expression of CD31, the expression increase of embryonic stem cells CD 31 of 10 μM treatment group was more significant (see FIG. 3). It was indicated that 10 μM 2,3-dihydro-3-hydroxymethyl-6-amino-[1,4]-benzoxazine can significantly induce embryonic stem cells to differentiate to vascular endothelial cells.

4. Detection of In Vitro Vascularization:

The embryonic stem cells after induction for ten days were seeded in 24-well cell culture plate paved with Matrigel in advance, the detection culture system was replaced for the cells and placed at 37° C., the cells were cultured at CO2 incubator for 4 hours to 72 hours, and the vascularization conditions were regularly observed. The normal group was set: embryonic stem cells which were cultured for ten days under the culture conditions of differentiation culture medium; solvent control group: embryonic stem cells which were cultured for ten days after DMSO was added under the culture condition of differentiation culture medium. Experimental group: embryonic stem cells which were cultured for ten days after 2,3-dihydro-3-hydroxymethyl-6-amino-[1,4]-benzoxazine was added under the culture condition of differentiation culture medium. The vascularization conditions of cells on Matrigel of all groups were observed with inverted phase contrast microscope respectively on the 6th hour, 12th hour, 24th hour and 48th hour.

Figure 4:
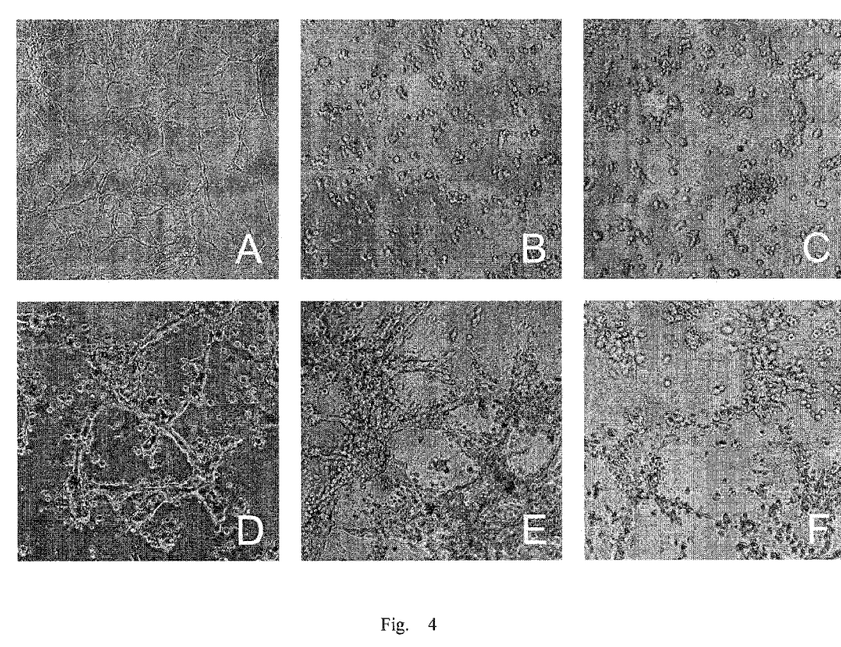
FIG. 4 shows the vascularization condition on Matrigel after embryonic stem cells are induced for ten days with 2,3-dihydro-3-hydroxymethyl-6-amino-[1,4]-benzoxazine, which is displayed under an inverted phase contrast microscope, under the culture condition that embryonic stem cells do not contain eukemia inhibitory factor.
Wherein:
A: A refers to human umbilical vein endothelial cells which are cultured on Matrigel for six hours as positive control;
B: The embryonic stem cells are naturally differentiated for ten days and are cultured for six hours on Matrigel under the culture condition that eukemia inhibitory factor is not contained.
C: The embryonic stem cells are differentiated for ten days and are cultured for six hours on Matrigel after DMSO is added under the culture condition that eukemia inhibitory factor is not contained.
D: The embryonic stem cells are induced for ten days and are cultured for six hours on Matrigel after 2,3-dihydro-3-hydroxymethyl-6-amino-[1,4]-benzoxazine with the concentration of 5 μM is added under the culture condition that eukemia inhibitory factor is not contained.
E: The embryonic stem cells are induced for ten days and are cultured for six hours on Matrigel after 2,3-dihydro-3-hydroxymethyl-6-amino-[1,4]-benzoxazine with the concentration of 10 μM is added under the culture condition that eukemia inhibitory factor is not contained.
F: The embryonic stem cells are induced for ten days and are cultured for six hours on Matrigel after 2,3-dihydro-3-hydroxymethyl-6-amino-[1,4]-benzoxazine with the concentration of 20 μM is added under the culture condition that eukemia inhibitory factor is not contained.

Solvent control group cells which were only added with DMSO under the culture condition of differentiation culture medium can hardly differentiate and form vessel-like structures on the Matrigel, and most of the embryonic stem cell aggregate into the colony with the extension of culture time. In contrast, the cells of the experiment group, which were added with 2,3-dihydro-3-hydroxymethyl-6-amino-[1,4]-benzoxazine with the concentration of 1~20 μM form varying degrees of cavity-like vessel-like structures on Matrigel, and the formed vessel-like structures were gradually thickened with the extension of culture time (see FIG. 4). Wherein, the 10 μM treatment group had particularly prominent vessel-like structures. The results showed that: in the detection of in vitro angiogenesis, the embryonic stem cells which were induced for ten days by 2,3-dihydro-3-hydroxymethyl-6-amino-[1, 4]-benzoxazine with the concentration of 10 μM had prominent angiogenesis effect on Matrigel.

5. Function Detection of Phagocytosis Dil-Ac-LDL (Acetylated Low-Density Lipoprotein Labeled by Dil):

The embryonic stem cells after induction for ten days were seeded in 24-well paved with gelatin, placed at 37° C., and cultured in CO2 incubator. After the cells adhered on the wall, the Dil-Ac-LDL diluted with medium culture was added into the culture plates, placed at 37° C., and cultured in CO2 incubator for six hours. The normal group was set: embryonic stem cells which were cultured for ten days under the culture condition of differentiation culture medium; Solvent control group: the embryonic stem cells which were cultured for ten days after DMSO was added under the culture condition of differentiation culture medium; experimental group: the embryonic stem cells which were cultured for ten days after 2,3-dihydro-3-hydroxy methyl-6-amino-[1,4]-benzoxazine with the concentration of 0.5 μM~40 μM was added under the culture condition of differentiation culture medium. After the completion of incubation, laser scanning confocal microscopy was used for observing the condition that the cells phagocytose Dil-Ac-LDL.

Figure 5:
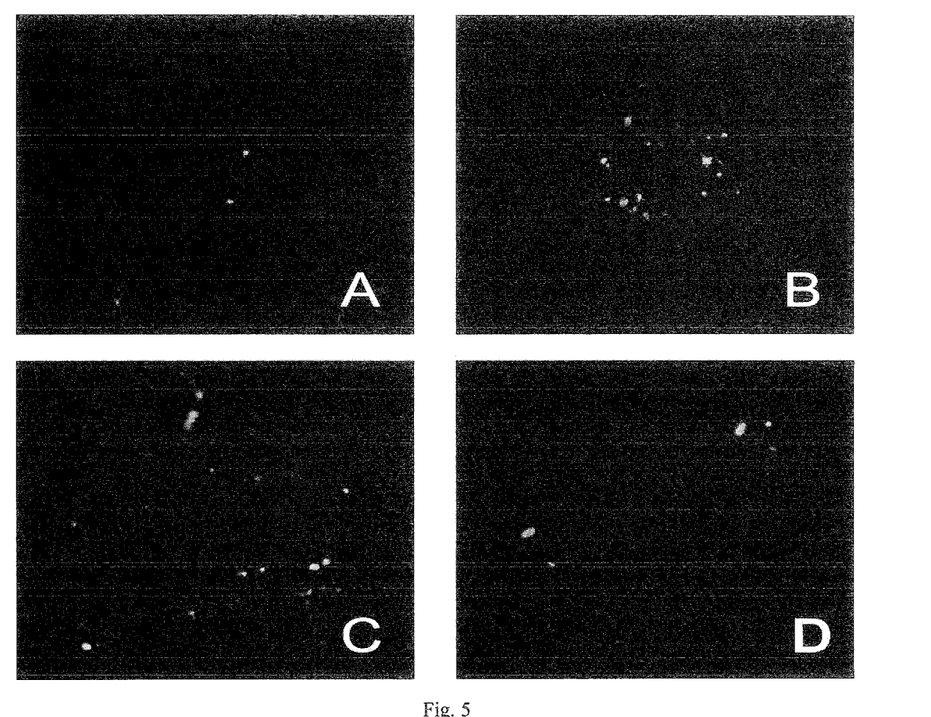
FIG. 5 shows the condition of phagocytosing Dil-Ac-LDL after embryonic stem cells are induced for ten days with 2,3-dihydro-3-hydroxymethyl-6-amino-[1,4]-benzoxazine, which is displayed under a confocal laser scanning microscope, under the culture condition that embryonic stem cells do not contain eukemia inhibitory factor.

The results showed that: compared with the control group, embryonic stem cells processed with 2,3-dihydro-3-hydroxymethyl-6-amino-[1,4]-benzoxazine with the concentration of 1 μM~20 μM in the experimental group can phagocytose Dil-Ac-LDL, wherein the phagocytosis condition in the 10 μM treatment group was particularly evident. (See FIG. 5) It was indicated that the embryonic stem cells induced with 2,3-dihydro-3-hydroxymethyl-6-amino-[1,4]-benzoxazine with the concentration of 10 μM has prominent effect of phagocytosing Dil-Ac-LDL.

From the above experiments and results, the following conclusions can be drawn:

The treatment of embryonic stem cells for five to ten days with 2,3-dihydro-3-hydroxymethyl-6-amino-[1,4]-benzoxazine with the concentration of 1 μM~20 μM under the culture condition of differentiation culture medium can prominently promote differentiation of mouse embryonic stem cells to vascular endothelial cells, the embryonic stem cells processed with 2,3-dihydro-3-hydroxymethyl-6-amino-[1,4]-benzoxazine with the concentration of 10 μM was particularly prominent. The vascularization experiment results on in vitro Matrigel showed that the embryonic stem cells induced for ten days with 2,3-dihydro-3-hydroxymethyl-6-amino-[1,4]-benzoxazine with the concentration of 10 μM can prominently form blood vessels in vitro. The detection results of function of phagocytosing Dil-Ac-LDL showed that the embryonic stem cells induced for ten days with 2,3-dihydro-3-hydroxymethyl-6-amino-[1,4]-benzoxazine with the concentration of 10 μM had prominent effect of phagocytosing Dil-Ac-LDL, thereby the invention provides theoretical and experimental basis for researching the mechanism of inducing embryonic stem cells to differentiate to vascular endothelial cells, the 2,3-dihydro-3-hydroxymethyl-6-amino-[1,4]-benzoxazine involved in the invention can be used as an effective tool for researching on molecular mechanism of differentiation of embryonic stem cells and vascularization, meanwhile, the invention lays foundation for researching and developing drugs about prompting vascularization.

BRIEF DESCRIPTION OF THE DRAWINGS

Wherein.

A: The embryonic stem cells are induced for ten days after after DMSO is added under the culture condition that eukemia inhibitory factor is not contained.

B: The embryonic stem cells are induced for ten days after 2,3-dihydro-3-hydroxymethyl-6-amino-[1,4]-benzoxazine with the concentration of 5 µM is added under the culture condition that eukemia inhibitory factor is not contained.

C: The embryonic stem cells are induced for ten days after 2,3-dihydro-3-hydroxymethyl-6-amino-[1,4]-benzoxazine with the concentration of 10 µM is added under the culture condition that eukemia inhibitory factor is not contained.

D: The embryonic stem cells are induced for ten days after 2,3-dihydro-3-hydroxymethyl-6-amino-[1,4]-benzoxazine with the concentration of 20 µM is added under the culture condition that eukemia inhibitory factor is not contained.

DETAILED DESCRIPTION

Next, embodiments are combined to further clarify the invention, wherein, the technicians of the major can adjust for implementation according to specific circumstances or relevant knowledge as for technical solutions which are not described in details in the invention or are similar with the method in the field.

The embodiment 1 relates to preparation of 2,3-dihydro-3-hydroxymethyl-6-amino-[1,4]-benzoxazine Iron powder (0.670 g, 12 mmol) was added into EtOH/H2O (v/v=6:1, 100 mL) solution of 2,4-dinitrophenyl glycidyl ether (0.480 g, 2 mmol) and acetic acid (1 mL, 17.5 mmol) at reflux temperature. The reaction mixture was refluxed continuously for 120 minutes, and cooled to room temperature, saturated Na2CO3 solution was used for adjusting pH=8, the solution was leached out with C salt for concentrating ethanol and water in the filtrate, and the solid ethanol was obtained (10 mL×4). Ethanol phase was dried with anhydrous MgSO4 and filtered to obtain crude products; the above crude products were separated with silica gel column chromatography (ethanol as developing agent), and 2,3-dihydro-3-hydroxymethyl-6-amino-[1,4]-benzoxazine (0.149 g, 42%) was prepared.

The embodiment 2 relates to detection of influence of 2,3-dihydro-3-hydroxymethyl-6-amino-[1,4]-benzoxazine on forms of embryonic stem cells;

The embryonic stem cells were evenly grown in a 24-well plate according to density of 2×104 cells/well, DMEM (high glucose) containing leukemia inhibitory factor, L-glutamine, streptomycin, β-mercaptoethanol, non-essential amino acids, nucleotides and 15% PBS was used for culturing for 24 hours, the waste liquid was discarded after the cells adhered on the wall, and the cells were cleaned with 1×PBS. A normal group was set: the normal group was cultured under the culture condition that leukemia inhibitory factor was removed; solvent control group: the group was cultured after DMSO was added under the culture condition that leukemia inhibitory factor was removed; experimental group: the group was cultured after 2,3-dihydro-3-hydroxymethyl-[1,4]-benzoxazine with the concentration of 0.5 µM, 1 µM, 5 µM, 10 µM, 20 µM, 30 µM and 40 µM was added under the culture condition that leukemia inhibitory factor was removed. The culture conditions: 37° C., CO2 incubator box for cultivation. The culture medium should be replaced everyday in a timing mode, and the cells were continuously cultured for ten days and then were observed under an inverted phase contrast microscope.

The results showed that: compared with the normal group and the solvent control group, the 1~20 µM treatment group in the experimental group was changed compared with the cell form of the control group, and the 2,3-dihydro-3-hydroxymethyl-6-amino-[1,4]-benzoxazine with the concentration of 10 µM can prominently prompt the embryonic stem cells to show the vascular endothelial form.

Embodiment 3

Detection of Vascular Endothelial Cell Marker (Flk-1)

The embryonic stem cells were evenly grown in a 48-well plate and cultured for 24 hours with DMEM (high glucose) containing leukemia inhibitory factor, L-glutamine, streptomycin, β-mercaptoethanol, non-essential amino acids, nucleotides and 15% FBS, the waste liquid was discarded after the cells adhered on the wall, and the cells were cleaned with 1×PBS. The normal group was set: the group was cultured under the culture condition that leukemia inhibitory factor was removed; solvent control group: the group was cultured after DMSO was added under the culture condition that leukemia inhibitory factor was removed; experimental group: the group was cultured after 2,3-dihydro-3-hydroxymethyl-6-amino-[1,4]-benzoxazine with the concentration of 0.5 µM, 1 µM, 5 µM, 10 µM, 20 µM, 30 µM and 40 µM was added under the culture condition that leukemia inhibitory factor was removed. The culture conditions: 37° C., CO2 incubator box for cultivation. The culture medium should be replaced everyday, the waste liquid is discarded 10 days later, the cells were fixed with 4% paraformal-dehyde for 15 minutes after being washed for three times with 0.1×PBS, Lowlenthal serum was sealed for 20 minutes after cleaning, the primary antibody of Flk-1 was added for incubation overnight at 4° C., 0.1×PBS was used for washing for three times, the second antibody was added for incubation at 37° C. for 40 minutes, the expression of endothelial cell marker—Flk-1 was observed with laser scanning confocal microscopy after cleaning.

The results showed that: the Flk-1 expression in 2 3-dihydro-3-hydroxymethyl-6-amino-[1,4]-benzoxazine with the concentration of 1 µM~20 µM experiment groups was increased, the cells processed with 10 µM 2 3-dihydro-3-hydroxymethyl-6-amino-[1,4]-benzoxazine had stronger Flk-1 expression compared with the normal group, the solvent control group and other groups of the experimental group. It is indicated that 10 µM 2,3-dihydro-3-hydroxymethyl-6-amino-[1,4]-benzoxazine can significantly induce embryonic stem cells to differentiate to vascular endothelial cells (see FIG. 2).

Embodiment 4

Detection of Vascular Endothelial Cell Marker (CD31)

The embryonic stem cells were evenly grown in a 6-well plate according to the density of 2×104 cells/well, and cultured for 24 hours with DMEM (high glucose) containing leukemia inhibitory factor, L-glutamine, streptomycin, β-mercaptoethanol, non-essential amino acids, nucleotides and 15% FBS, the waste liquid was discarded after the cells adhered on the wall, and the cells were cleaned with 1×PBS. The normal group was set: the group was cultured under the culture condition that leukemia inhibitory factor was removed; solvent control group: the group was cultured after DMSO was added under the culture condition that leukemia inhibitory factor was removed; experimental group: the group was cultured after 2,3-dihydro-3-hydroxymethyl-6-amino-[1,4]-benzoxazine with the concentration of 0.5 µM, 1 µM, 5 µM, 10 µM, 20 µM, 30 µM and 40 µM was added under the culture condition that leukemia inhibitory factor was removed. The culture conditions: 37° C., CO2 incubator box for cultivation. The culture medium should be replaced everyday, and the cells should be continuously cultured for ten days. The total protein of each group of cells was distilled with cell lysate. The protein samples were denatured for 5 min at 100° C., glue was removed then, the protein was transferred on the PVDF film after completion, the PBS/t solution containing 5% skimmed milk powder was used for sealing for one hour at room temperature. The PBS/t solution containing 3% bovine serum almbumin was used for diluting the primary anti-body (1:5000), and incubated overnight with the PVDF film containing target protein at 4° C. PBS/t was used for dipping the film twice 5 min each time. PBS was used for diluting the secondary antibody (1:5000) and the cells were incubated for one hour at room temperature, the film was dipped with PSB for three times and 5 min each time. ECL chromogenic reagent was evenly coated on the PVDF film containing target protein ad reacted for five minutes, excessive Chromogenic reagent was removed, and the cells were placed together with the film in a dark box for five minutes to finish film colour development.

The results showed that: the CD31 expression in 2 3-dihydro-3-hydroxymethyl-6-amino-[1,4]-benzoxazine with the concentration of 1 µM~20 µM experiment groups was increased, the cells processed with 10 µM 2 3-dihydro-3-hydroxymethyl-6-amino-[1,4]-benzoxazine had stronger CD31 expression compared with the solvent control group and other groups of the experimental group. It is indicated that 10 µM 2,3-dihydro-3-hydroxymethyl-6-amino-[1,4]-benzoxazine can significantly induce embryonic stem cells to differentiate to vascular endothelial cells (see FIG. 3).

Embodiment 5

Detection of In Vitro Vascularization

The embryonic stem cells were evenly grown in a 24-well plate according to the density of 2×104 cells/well and cultured for 24 hours with DMEM (high glucose) containing leukemia inhibitory factor, L-glutamine, streptomycin, β-mercaptoethanol, non-essential amino acids, nucleotides and 15% FBS, the waste liquid was discarded after the cells adhered on the wall, and the cells were cleaned with 1×PBS. The normal group was set: the group was cultured under the culture condition that leukemia inhibitory factor was removed; solvent control group: the group was cultured after DMSO was added under the culture condition that leukemia inhibitory factor was removed; experimental group: the group was cultured after 2,3-dihydro-3-hydroxymethyl-6-amino-[1,4]-benzoxazine with the concentration of 0.5 µM, 1 µM, 5 µM, 10 µM, 20 µM, 30 µM and 40 µM was added under the culture condition that leukemia inhibitory factor was removed. The culture conditions: 37° C., CO2 incubator box for cultivation. The culture medium should be replaced everyday, the cells were continuously cultured for ten days, then, the cells were placed in the 24-well cell culture plate paved with Matrigel and placed at 37° C., the cells were incubated in the CO2 culture box for 60 minutes. The cells of each group were suspended in the DMEM (high glucose) culture medium containing no factor according to the density of 4-5×104 cells/well, and inoculated in the 24-well cell culture plate paved with Matrigel. The cell culture plate was placed at 37° C. in a CO2 culture box for culturing for 4 to 96 hours. The vascularization conditions of the blood vessel endothelial cells on the Matrigel were observed under an inverted phase contract microscope respectively on the 6th hour, 12th hour, 24th hour and 48th hour.

The results showed that: In the detection of in vitro vascularization, the cells of the experimental group of 2,3-dihydro-3-hydroxymethyl-6-amino-[1,4]-benzoxazine with the concentration of 1-20 µM can form varying degrees of cavity-like vessel-like structures on Matrigel, wherein, the embryonic stem cells induced with 2,3-dihydro-3-hydroxymethyl-6-amino-[1,4]-benzoxazine with the concentration of 10 µM can prominently form blood vessels on Matrigel 10 µM treatment group (see FIG. 4).

Embodiment 6

Detection of Function of Phagocytosing Dil-Ac-LDL

The embryonic stem cells were evenly grown in a 24-well plate according to the density of 2×104 cells/well and cultured for 24 hours with DMEM (high glucose) containing leukemia inhibitory factor, L-glutamine, streptomycin, β-mercaptoethanol, non-essential amino acids, nucleotides and 15% FBS, the waste liquid was discarded after the cells adhered on the wall, and the cells were cleaned with 1×PBS. The normal group was set: the group was cultured under the culture condition that leukemia inhibitory factor was removed; solvent control group: the group was cultured after DMSO was added under the culture condition that leukemia inhibitory factor was removed; experimental group: the group was cultured after 2,3-dihydro-3-hydroxymethyl-6-amino-[1,4]-benzoxazine with the concentration of 0.5 µM, 1 µM, 5 µM, 10 µM, 20 µM, 30 µM and 40 µM was added under the culture condition that leukemia inhibitory factor was removed. The culture conditions: 37° C., CO2 incubator box for cultivation. The culture medium should be replaced everyday, the cells were continuously cultured for ten days, the Dil-Ac-LDL was diluted into 10 µl/ml with fresh differential culture medium and added into the cell culture plate, it is incubated for six hours at 37° C. in the CO2 culture box. The conditions of phagocytosing Dil-Ac-LDL were detected with laser confocal microscopy.

The results showed that: In the detection of function of phagocytosing Dil-Ac-LDL, the cells processed with 2,3-dihydro-3-hydroxymethyl-6-amino-[1,4]-benzoxazine with the concentration of 1-20 µM can phagocytose Dil-Ac-LDL the embryonic stem cells induced with 2,3-dihydro-3-hydroxymethyl-6-amino-[1,4]-benzoxazine with the concentration of 10 µM can prominently phagocytose Dil-Ac-LDL (see FIG. 5).

What is claimed is:
1. A method of inducing embryonic stem cells to differentiate to functional vascular endothelial cells, comprising culturing the embryonic stem cells with a culture medium comprising 2,3-dihydro-3-hydroxymethyl-6-amino-[1,4]-benzoxazine at a concentration of from 1 to 20 µM.
2. The method of claim 1, wherein the concentration of 2,3-dihydro-3-hydroxymethyl-6-amino-[1,4]-benzoxazine is 10 µM.

3. The method of claim 1, wherein the embryonic stem cells are mouse embryonic stem cells.

4. The method of claim 2, wherein the embryonic stem cells are mouse embryonic stem cells.

* * * * *